United States Patent [19]

Nakao et al.

[11] Patent Number: 5,015,249
[45] Date of Patent: May 14, 1991

[54] ENDOSCOPIC STAPLING DEVICE AND METHOD

[76] Inventors: Naomi L. Nakao, 303 E. 57th St., New York, N.Y. 10022; Peter J. Wilk, 185 W. End Ave., New York, N.Y. 10023

[21] Appl. No.: 456,960

[22] Filed: Dec. 26, 1989

[51] Int. Cl.⁵ .............................................. A61B 17/00
[52] U.S. Cl. ..................................... 606/142; 227/901
[58] Field of Search .............. 606/138, 142; 227/178, 227/175, 179, 180, 904, 901

[56] References Cited

U.S. PATENT DOCUMENTS

| | | | |
|---|---|---|---|
| 943,263 | 12/1909 | Morawek . | |
| 1,510,416 | 9/1924 | Pietz | 606/205 |
| 2,113,246 | 4/1938 | Wappler . | |
| 2,968,041 | 1/1961 | Skold | 227/904 |
| 3,378,010 | 4/1968 | Codling | 606/157 |
| 3,518,993 | 7/1970 | Blake | 227/904 |
| 3,882,854 | 5/1975 | Hulka et al. | 227/904 |
| 3,958,576 | 5/1976 | Komiya | 606/140 |
| 4,038,987 | 8/1977 | Komiya | 606/ |
| 4,367,746 | 1/1983 | Derechinsky | 227/904 |
| 4,394,864 | 7/1983 | Sandhaus | 606/142 |
| 4,446,865 | 5/1984 | Jewusiak | 606/158 |
| 4,485,817 | 12/1984 | Swiggett | 227/180 |
| 4,496,090 | 1/1985 | Crerier et al. | 227/19 |
| 4,681,107 | 7/1987 | Kees, Jr. | 606/142 |
| 4,706,668 | 11/1987 | Backer | 606/142 |
| 4,714,075 | 12/1987 | Krauter | 128/4 |
| 4,735,194 | 4/1988 | Stiegmann | 128/6 |
| 4,759,364 | 7/1988 | Boebel | 606/142 |
| 4,796,627 | 1/1989 | Tucker | 606/143 |
| 4,821,721 | 4/1989 | Chin et al. | 606/143 |
| 4,841,888 | 6/1989 | Mills et al. | 606/145 |
| 4,880,015 | 11/1989 | Nierman | 128/751 |
| 4,887,612 | 12/1989 | Esser | 128/751 |
| 4,945,920 | 8/1990 | Clossick | 128/751 |

Primary Examiner—Stephen C. Pellegrino
Assistant Examiner—Gary Jackson
Attorney, Agent, or Firm—R. Neil Sudol; Henry D. Coleman

[57] ABSTRACT

A surgical stapling apparatus comprises an endoscope, an elongate flexible tubular member slidably disposed in a biopsy channel of the endoscope, an elongate flexible rod member slidably disposed inside the tubular member and a staple disposed in a closed configuration inside the endoscope biopsy channel distally of the distal end of the rod member. The staple is releasably connected to the rod member. In operating the stapling apparatus, the endoscope is inserted through an aperture in a patient's body, the endoscope's optics being used to locate a surgical site. Upon finding the surgical site, a surgeon pushes the flexible rod in the distal direction to eject the staple from the endoscope biopsy channel. Upon ejection, the staple is opened, either through the action of its own internal forces or through the action of forceps jaws operated by the surgeon via an additional tubular member slidably disposed in the biopsy channel about the first tubular member. The rod is then pushed further in the distal direction to move the staple towards a blood vessel to be ligated or an opening to be closed. Upon sufficient engagement of the staple with the vessel or internal body tissues, the first tubular member is pushed in the distal direction to engage the staple legs and collapse them towards one another. The rod and the first tubular member are then retracted into the endoscope biopsy channel and the endoscope subsequently removed from the patient's body.

35 Claims, 10 Drawing Sheets

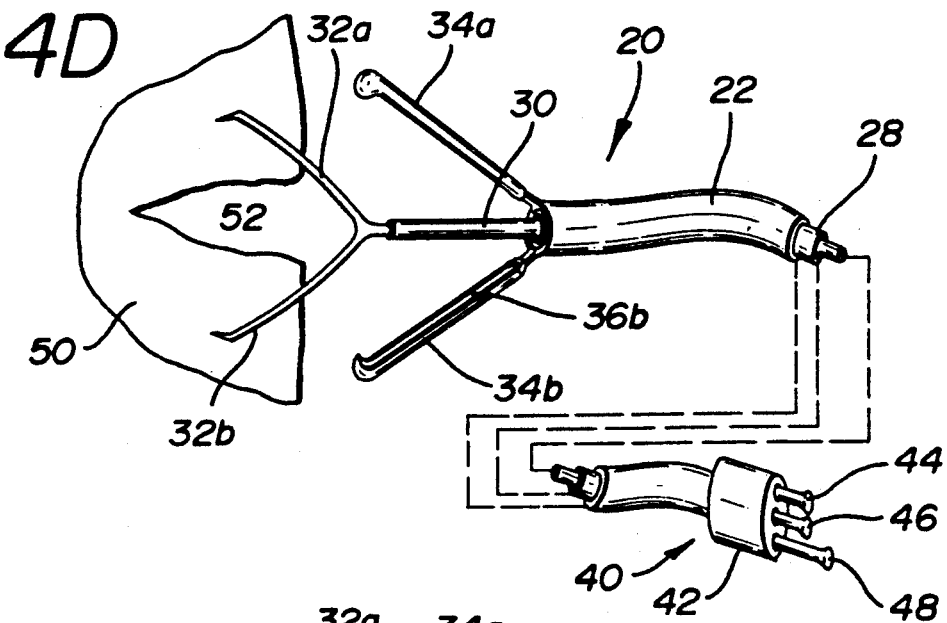
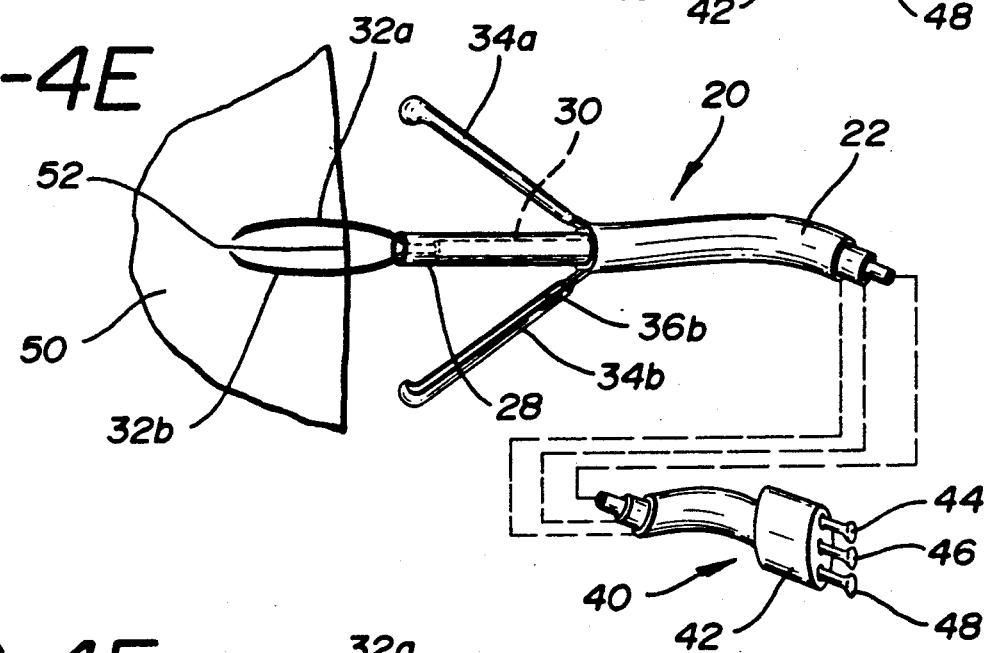
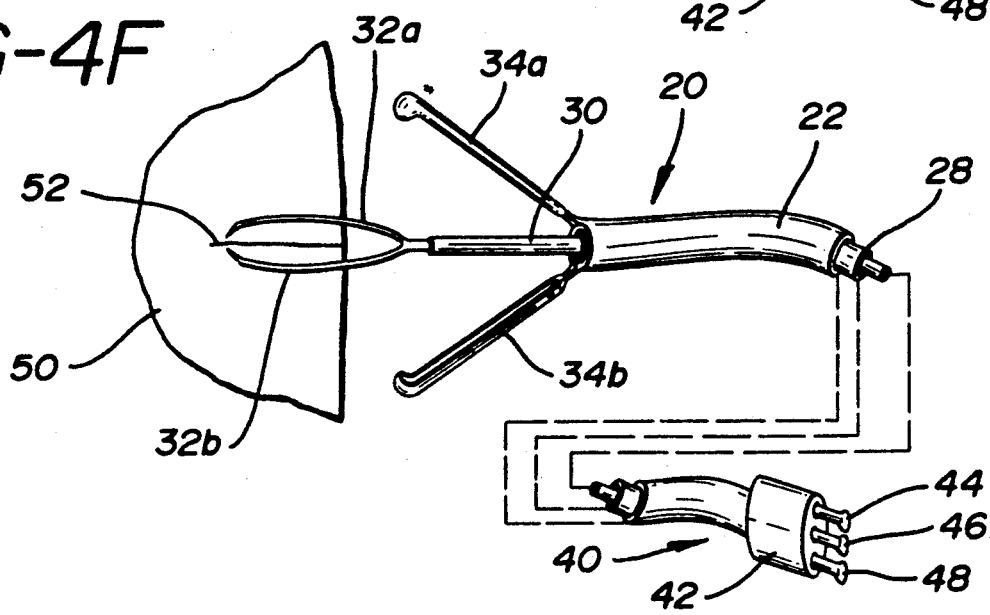

ENDOSCOPIC STAPLING DEVICE AND METHOD

BACKGROUND OF THE INVENTION

This invention relates to an endoscopic stapling device. More particularly, this invention relates to a device usable with an endoscope for performing a stapling operation on a patient's internal body tissues at a surgical site not visible to the unaided eye. This invention also relates to a surgical procedure utilizing an endoscope. The invention also involves a surgical staple and an associated staple holder or package.

Conventional surgical techniques for repairing tissue injuries such as hernias and perforated ulcers, for closing other openings in internal body tissues and for ligating tubular body organs such as sperm ducts and Fallopian tubes, generally require that an extensive incision be made in the patient's abdominal wall. Such an operation is generally traumatic to the patient, involves considerable surgeon time and requires a relatively lengthy convalescence. This is the case even though only one or a small number of sutures is required to repair the injury or tie off the vessel.

OBJECTS OF THE INVENTION

An object of the present invention is to provide a surgical procedure for closing openings internal to a patient's body, which is less invasive than conventional surgical closure methods.

Another object of the present invention is to provide such a surgical procedure which is quicker than conventional surgical procedures and which reduces the typical postoperative convalescence period.

A related object of the present invention is to provide an improved surgical closure procedure using an endoscope.

Another object of the present invention is to provide a stapling device usable with an endoscope.

An associated object of the present invention is to provide an endoscopic stapling device.

Another, more particular, object of the present invention is to provide a staple usable with such an endoscopic stapling device.

A further particular object of the present invention is to provide a staple package for use with such an endoscopic stapling device.

SUMMARY OF THE INVENTION

A method for performing a surgical operation on internal body tissues of a patient comprises, in accordance with the present invention, the steps of (a) inserting a tubular endoscope member through an aperture in the patient's body, (b) using the endoscope to visually locate the internal body tissues inside the patient's body, and (c) upon locating the surgical site, pushing an elongate flexible rod member in a distal direction through a biopsy channel in the tubular endoscope member to eject a staple stored in a closed configuration inside the channel at a distal end of the tubular endoscope member. Upon ejection of the staple from the biopsy channel, the staple is opened from the closed configuration to an opened configuration. The opened staple is then pushed towards the internal body tissues. Upon contact of the opened staple with the internal body tissues, the staple is closed about a portion of the internal body tissues and, upon staple closure, the tubular endoscope member is withdrawn from the patient's body though the aperture.

Pursuant to further features of the present invention, the step of pushing the opened staple comprises the step of pushing the elongate flexible rod member further in the distal direction, while the step of closing comprises the step of pushing an elongate flexible inner tubular member, disposed in the channel about the rod member, in the distal direction to engage legs of the staple and thereby collapse the legs towards one another. In an additional step in a method in accordance with the present invention, the rod member and the tubular member are retracted into the biopsy channel after the closure of the staple and prior to the withdrawal of the endoscope from the patient's body.

In a preferred of two alternative embodiments of the present invention, the step of opening the staple is accomplished by pulling the legs of the staple apart with a pair of forceps jaws releasably connected to the legs. In another of the alternative embodiments, the staple is spring biased towards an opened configuration, the step of opening being accomplished automatically by internal forces in the staple upon ejection of the staple from the biopsy channel of the endoscope. In the latter embodiment, the staple legs are locked to one another by a latching mechanism upon closure of the staple at the surgical site.

The endoscope may be a fiber optic flexible esophagogastroscope (upper endoscope) inserted through the mouth and esophagus of the patient or a thin fiber optic flexible colonoscope inserted through the patient's rectum. In another surgical procedure, exemplarily used in repairing herniated tissues, the patient's abdomen is pierced by a trocar and the endoscope is inserted through a lumen which remains in the aperture formed by the trocar.

In yet another step performed in a method in accordance with the present invention, the internal body tissues (a vessel or about an opening) are gripped and squeezed together. The gripping and squeezing may be done with a forceps operated preferably via an elongate flexible tubular member disposed in the endoscope biopsy channel about the staple-closing tubular member.

A surgical stapling instrument in accordance with the present invention comprises an elongate flexible tubular member, an elongate flexible rod member slidably disposed inside the tubular member, a staple, and means for opening the staple upon an expulsion thereof from the tubular member by a distally directed motion of the rod member. The tubular member has a diameter sufficiently small so that it is slidably insertable into a biopsy channel extending longitudinally through a flexible tubular endoscope member. In addition, the staple disposed in a closed configuration at least partially inside the tubular member distally of a distal end of the rod member.

A surgical stapling instrument in accordance with the invention may be sold either in combination with an endoscope (fiber-optic, or video) or separately, for retrofit to existing endoscopes.

In a preferred embodiment of the present invention, the means for opening the staple includes an additional flexible tubular member slidably disposed around the elongate flexible tubular member, the additional flexible tubular member being provided at a distal end with a pair of forceps jaws releasably connected to legs of the staple.

Pursuant to particular features of this embodiment, the jaws are provided on inwardly facing surfaces with grooves and recesses, the staple legs being seated in the grooves in a closed configuration of the staple and the forceps jaws, and the free ends of the staple legs being held in the recesses in the closed configuration of the staple and the forceps jaws.

Pursuant to an alternative embodiment of the present invention, the means for opening the staple is inherent in the staple itself and includes a spring bias construction of the staple. Pursuant to this embodiment of the invention, the staple is advantageously provided with a pair of interlocking hook elements on the legs or other means for locking the staple in a closed configuration upon a closing of the staple by a distally directed motion of the elongate flexible tubular member subsequent to a distally directed motion of the rod member pushing the staple, in an opened configuration thereof, into or about body tissues to be clamped by the staple.

In accordance with another feature of the present invention, the staple and the flexible rod member are provided with cooperating elements for releasably attaching a proximal end of the staple to a distal end of the rod member. The cooperating element on the staple is disposed preferably at the bight of the staple and takes the form of a linear projection extending in a proximal direction from the bight in a prefiring configuration of the staple. The cooperating element on the flexible rod member then takes the form of a longitudinally extending recess in the distal end of the rod member. More specifically, the projection is planar and the recess is polygonal in transverse cross-section.

Another surgical stapling instrument in accordance with the present invention comprises an elongate flexible tubular member, an elongate flexible rod member slidably disposed inside the elongate flexible tubular member, a first actuator component such as a handle operatively connected to the tubular member for sliding that member through the biopsy channel, and a second actuator component operatively connected to the rod member for sliding that member through the tubular member. The tubular member has a diameter sufficiently small so that it is slidably insertable into a biopsy channel extending longitudinally through a flexible tubular endoscope member. In addition, the rod member is provided at a distal end with a connector element for releasably connecting the rod to a staple.

Pursuant to a specific embodiment of the invention, an additional flexible tubular member is slidably disposed around the elongate flexible tubular member. The additional tubular member is sufficiently small to be slidably insertable into the biopsy channel of an endoscope. The additional tubular member is provided at a distal end with a pair of forceps jaws. Preferably, the forceps jaws are provided on inwardly facing surfaces with grooves for receiving legs of a staple and with recesses for receiving free ends of such a staple.

Pursuant to this specific embodiment of the invention, another actuator component is operatively connected to the additional flexible tubular member for sliding that member through the biopsy channel of an endoscope.

A surgical staple in accordance with the present invention comprises a pair of legs, a bight portion connected to each of the legs at one end thereof, and a projection connected to the bight portion and extending in a direction opposite the legs. The projection includes means for releasably attaching the staple to an elongate rod. The projection may assume any of a number of different geometric configurations, including spherical, planar, and cross-sectionally polygonal.

The surgical staple is advantageously provided with a pair of interlocking hooks or other elements on the legs for locking the staple in a closed configuration.

A surgical staple package in accordance with the present invention comprises a container provided with a plurality of recesses having an inside diameter, a plurality of sleeves disposed in the recesses, and a plurality of staples each seated in a respective one of the sleeves. The sleeves have a common outside diameter smaller than the inside diameter of the container recesses so than an annular space is formed between each of the sleeves and the walls defining the respective one of the recesses. Each of the staples is provided with a connector element for releasably connecting the respective staple to distal end of a flexible rod member of an endoscopic stapling device.

An endoscopic stapling device in accordance with the present invention enables a non-invasive closure of internal openings and vessels. Many surgical operations can be accomplished without the formation of any new opening in the external body tissues. In such cases, the endoscopic stapling device is operated through a natural body aperture (the mouth or rectum). In other cases, the only opening which is needed is one just large enough to accommodate a fiber optic endoscope. Such an operation would be useful, for example, to repair hernias.

Use of an endoscopic stapling device in accordance with the present invention, therefore, minimizes operation time, as well as the hospital stay. Costs are accordingly reduced.

BRIEF DESCRIPTION OF THE DRAWING

FIGS. 4A-4I are partially schematic, partial perspective views, taken from the side and on a reduced scale, of an endoscopic stapling device in accordance with the present invention, showing successive stages in the application of a surgical staple to internal body tissues.

DETAILED DESCRIPTION

Figure 1:
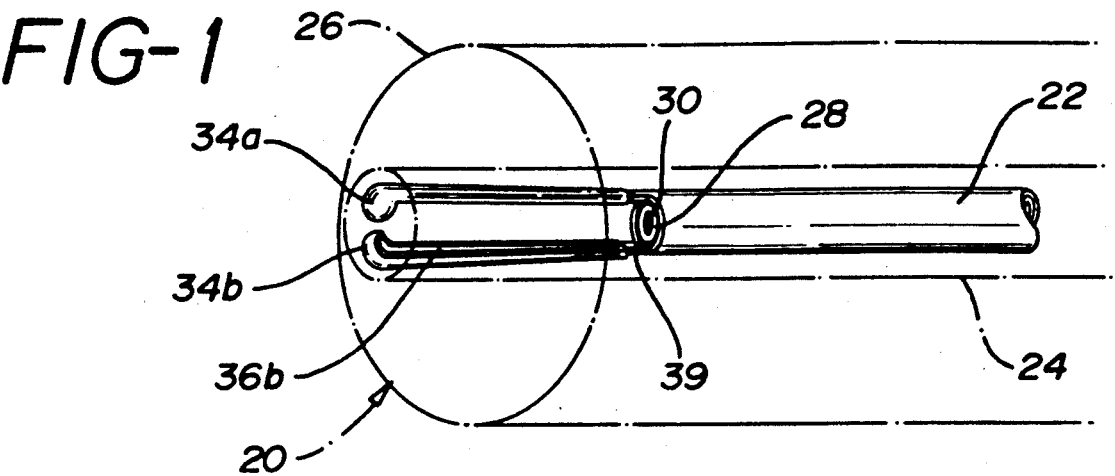
FIG. 1 is a partial perspective view, taken from the side, of an endoscopic stapling device in accordance with the present invention, showing the device in a prefiring configuration without a loaded staple.
Figure 2:
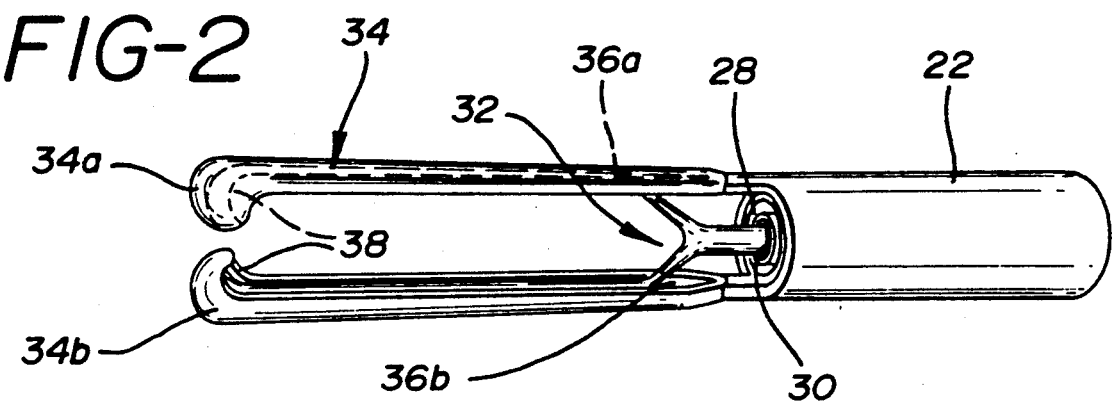
FIG. 2 is a partial perspective view, similar to FIG. 1, showing the endoscopic stapling device in the prefiring configuration with a loaded staple in a closed configuration.

As illustrated in FIGS. 1 and 2, an endoscopic stapling device 20 comprises an outer elongate flexible tubular member 22 having a diameter sufficiently small so that the tubular member is slidably insertable into a biopsy channel 24 extending longitudinally through a flexible tubular endoscope member 26. Endoscopic stapling device 20 further comprises an inner elongate flexible tubular member 28 slidably disposed inside tubular member 22 and an elongate flexible rod member 30 slidably disposed inside inner tubular member 28. In the prefiring configuration of FIG. 2, a staple 32 is disposed in a closed configuration at least partially inside inner tubular member 28 distally of a distal end of rod member 30.

Figure 3:
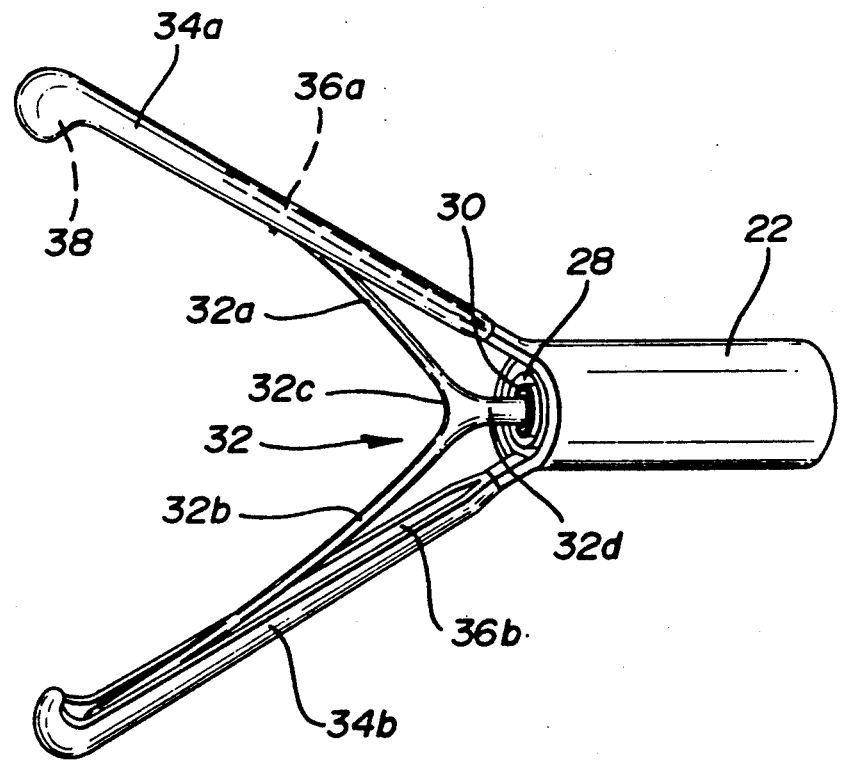
FIG. 3 is a partial perspective view, taken from the side, of the endoscopic stapling device of FIGS. 1 and 2, showing the device in an initial firing stage with an opened staple.

Outer tubular member 22 is provided at a distal end with a forceps 34 including a pair of spring loaded jaws 34a and 34b. As shown in FIGS. 2 and 3, staple 32 includes a pair of legs 32a and 32b seated in the prefiring configuration of the endoscopic stapling device 20 in grooves 36a and 36b provided on inwardly facing surfaces of forceps jaws 34a and 34b. As described hereinafter with reference to FIGS. 4A–4I, jaws 34a and 34b serve to open staple 32 upon an ejection thereof from inner tubular member 28 by a distally directed motion of rod member 30. Jaws 34a and 34b are releasably connected to staple legs 32a and 32b so that staple 32 becomes detached from forceps 34 upon the attainment of a predetermined angular displacement between jaws 34a and 34b. More particularly, the free ends of staple legs 32a and 32b are held in the prefiring configuration of the endoscopic stapling device in cup-shaped recesses 38 formed at the free ends of jaws 34a and 34b.

Staple 32 further includes a bight portion 32c joining staple legs 32a and 32b to one another and to a planar projection 32d extending away from bight portion 32c in a direction opposite legs 32a and 32b. In the staple loaded configuration of FIG. 2, projection 32d is received in a cross-sectionally rectangular recess or opening 39 at the distal end of rod member 30.

It is to be noted that projection 32d and recess 39 may have any of several different geometric shapes. In particular, other polygonal cross-sections can be used.

As shown in FIGS. 4A through 4I, endoscopic stapling device 20 includes an assembly 40 at its proximal end for enabling the operation of the device by a surgeon during an operation. Assembly 40 includes a housing or casing member 42 mountable to endoscope 26 at a proximal end thereof. Projecting from casing 42 are a plurality of handles or knobs 44, 46 and 48 which are mechanically connected to outer tubular member 22, rod member 30 and inner tubular member 28, respectively, for enabling the sliding of those members along biopsy channel 24 by a surgeon or other authorized operator. FIGS. 4A through 4I show the positions of handles 44, 46 and 48 corresponding to the operative configurations of outer tubular member 22, rod member 30, inner tubular member 28, and staple 32 shown in the respective drawing figures.

Figure 4A:
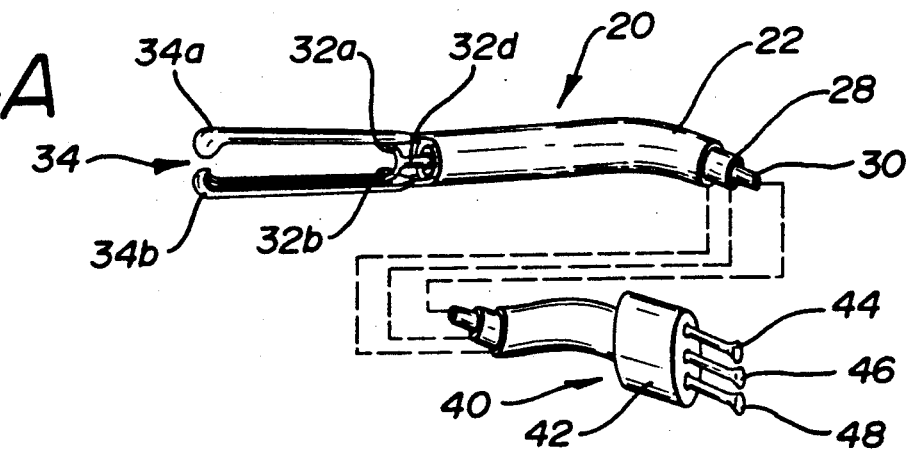
Figure 4B:
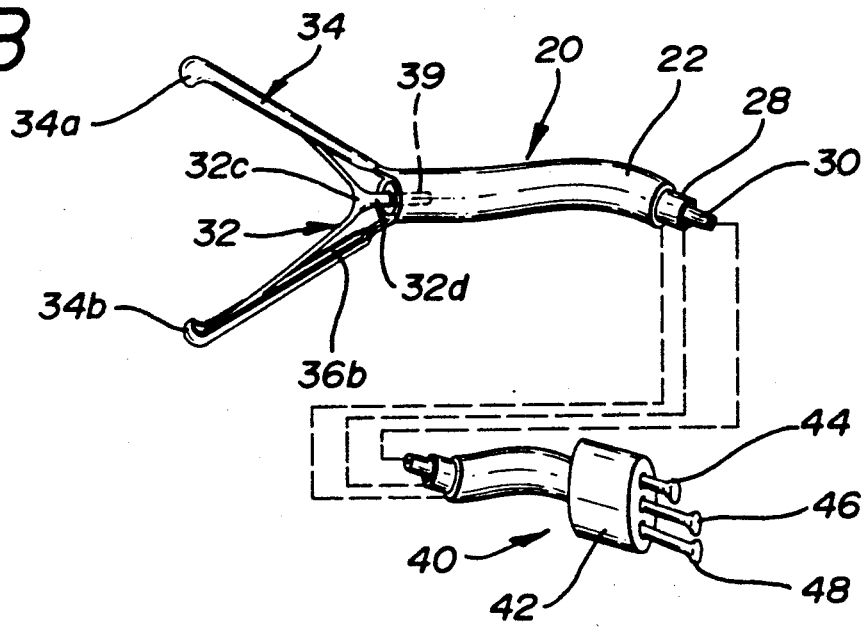

FIGS. 4A and 4B are similar to FIGS. 2 and 3. FIG. 4A shows endoscopic stapling device 20 in a prefiring configuration in which outer tubular member 22, inner tubular member 28, rod 30 and staple 32 are all located in biopsy channel 24 of endoscope 26. More specifically, staple 32 is disposed in a closed prefiring configuration distally of rod member 30 and inside tubular member 28 at the distal end thereof. Endoscope 26 has already been inserted through an aperture (not illustrated) in a patient's body (not shown) and has been used to visually locate in the patient's body the internal body tissues upon which a stapling operation is to be performed. The internal body tissues may be a vessel or duct which needs to be closed or perhaps an opening in the stomach wall.

Figure 4C:
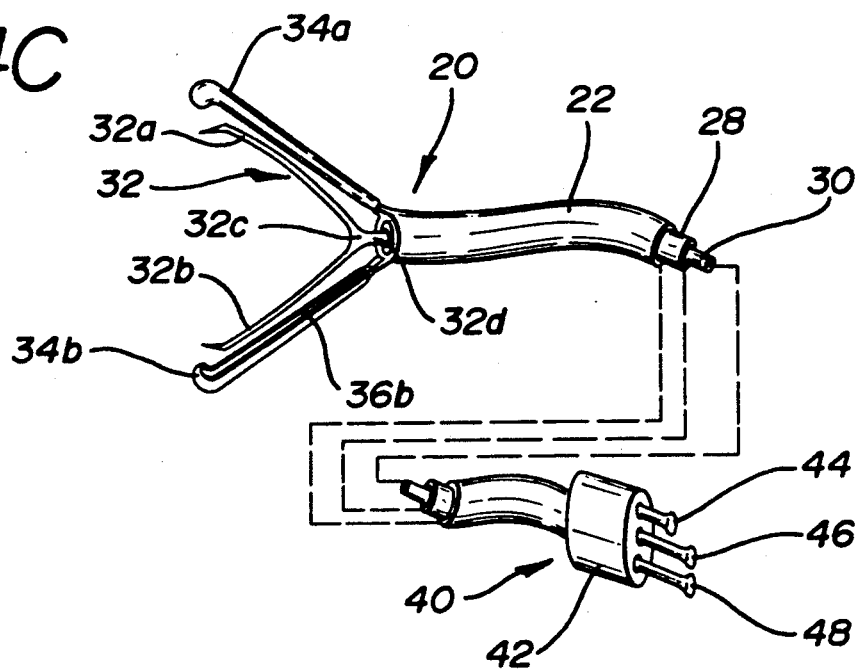
Figure 4G:
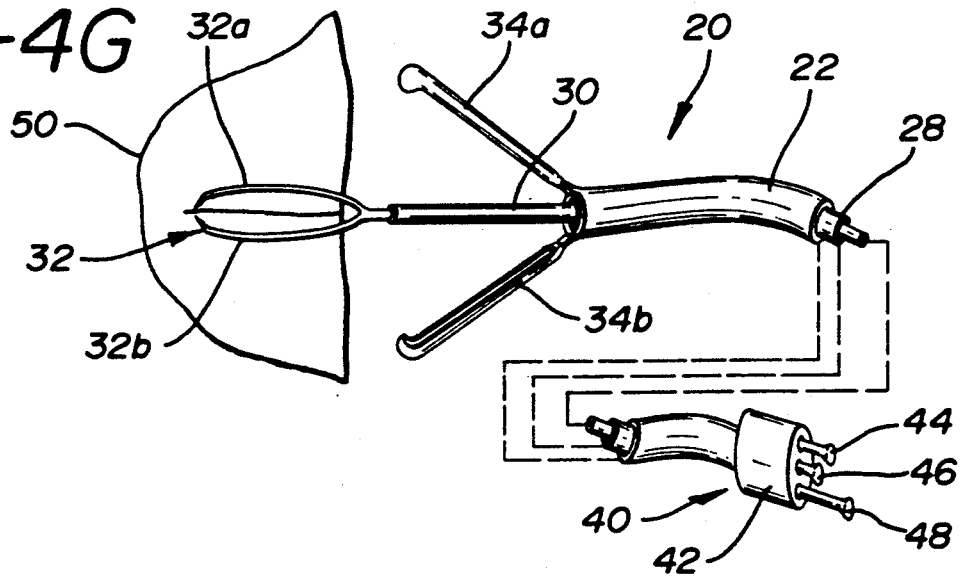

Upon the locating of the surgical site, tubular outer member 22 and rod member 30 are pushed in the distal direction through biopsy channel 24 to eject staple 32 from tubular member 28. During this distal motion, jaws 34a and 34b pivot away from one another and pull apart staple legs 32a and 32b, as shown in FIG. 4B. Upon a further outward pivoting of jaws 34a and 34b, the free ends of legs 32a and 32b slip out from recesses 38 at the distal ends of grooves 36a and 36b. Staple 32 is now in a released, opened configuration, as depicted in FIG. 4C.

In the next step of a surgical procedure using endoscopic stapling device 20, rod member 30 is pushed further in the distal direction to move opened staple 32 towards internal body tissues 50 having an opening 52 previously detected through the optical pathway (not illustrated) of endoscope 26. FIG. 4D shows staple 32 substantially embedded in the body tissues 50 in a region about opening 52.

Upon the embedding of opened staple 32 in internal body tissues 50, inner tubular member 28 is pushed in the distal direction to engage staple legs 32a and 32b and thereby close the staple about opening 52. The distal motion of inner tubular member 28 relative to rod member 30 and staple 32 bends legs 32a and 32b about bight portion 32c, causing staple 32 to assume a closed, tissue-clamping configuration shown in FIG. 4E.

In a subsequent step shown in FIG. 4F, inner tubular member 28 is retracted into biopsy channel 24. In an optional step depicted in FIG. 4G, rod member 30 may be moved even further in the distal direction to push staple 32 further into tissues 50. This step serves to limit the extent that the staple projects from tissues 50.

Figure 4H:
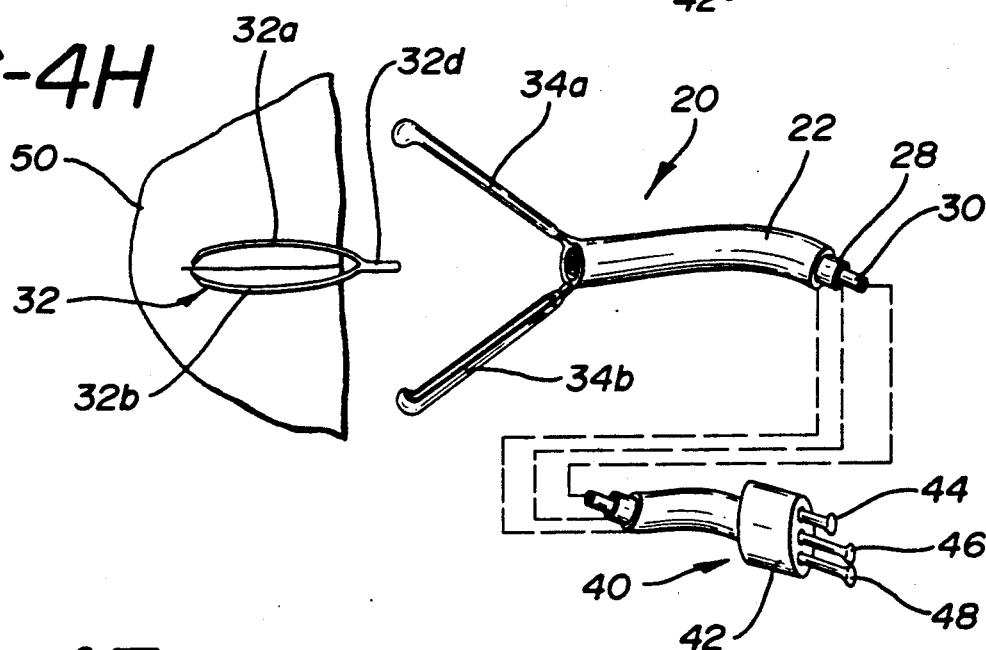
Figure 4I:
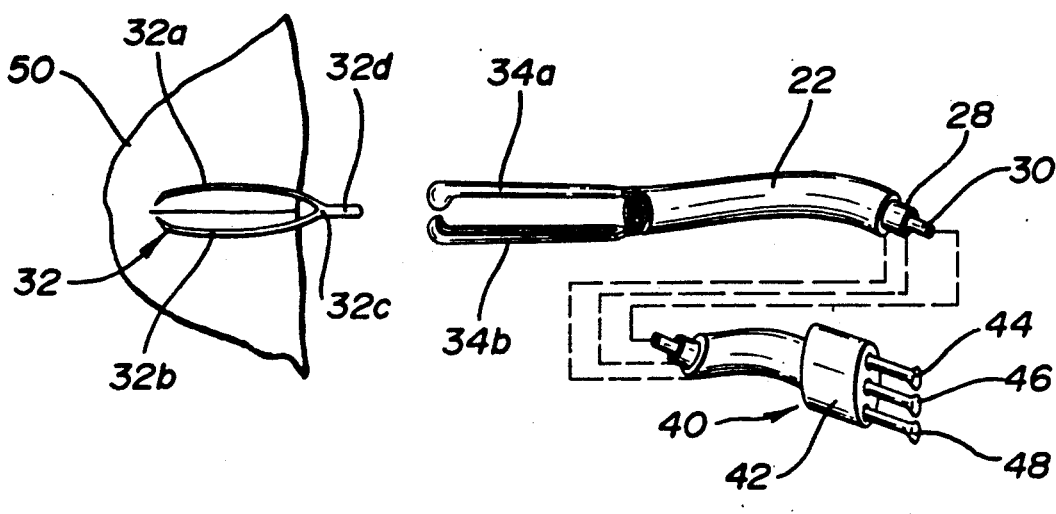

Upon a satisfactory disposition of staple 32 in tissues 50, whereby opening 52 is stapled closed, rod member 30 is retracted into inner tubular member 28 (FIG. 4H). Outer tubular member 22 is then moved in the proximal direction into biopsy channel 24, jaws 34a and 34b being pivoted towards one another during the proximally directed stroke of outer tubular member 22. The pivoting of jaws 34a and 34b is effectuated by a camming action when the jaws slide past the rim or lip at the distal end of biopsy channel 24.

Upon the completion of the stapling operation, outer tubular member 22, inner tubular member 28 and rod member 30 are all disposed in biopsy channel 24, so that the distal ends of those members do not extend beyond the distal end of the channel. The entire endoscopic instrument is then withdrawn from the patient's body through the aperture through which it was introduced. That aperture may take the form of a natural body opening. Alternatively, the endoscope introduction aperture may be formed through the use of a trocar. Such a procedure can be followed, for example, to repair a hernia through a small opening in the abdominal wall.

Figure 5:
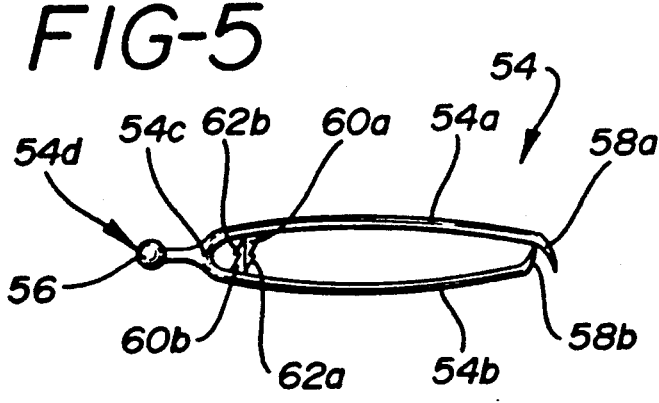
FIG. 5 is a side elevational view, on an enlarged scale, of a staple for use in an endoscopic stapling device in accordance with the present invention, showing the staple in a prefiring closed configuration.
Figure 6:
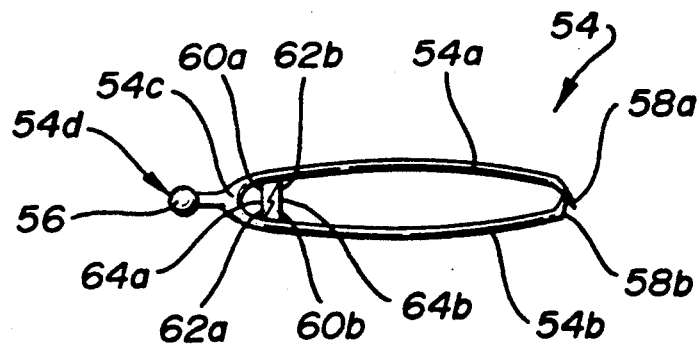
FIG. 6 is a side elevational view of the staple of FIG. 5, showing the staple in a closed, postfiring configuration.

As illustrated in FIGS. 5 and 6, a staple 54 for an endoscopic stapling device in accordance with the present invention includes a pair of legs 54a and 54b joined by a bight section 54c and provided on a side of the bight section opposite the legs with a projection 54d terminating in a knob or ball 56. Each leg 54a and 54b is provided at a free end with a respective inwardly turned foot 58a and 58b. In addition, on their inwardly facing sides, legs 54a and 54b are provided towards the proximal end of the staple with interlocking finger elements 60a and 60b having barbs or hooks 62a and 62b which cooperate with one another to lock the staple in a closed configuration at the end of a stapling operation.

Staple 54 is spring biased, by virtue of the inherent structural characteristics of its preferably metallic material, towards an opened (legs spread) configuration. The material and dimensions of staple 54 are selected so that the staple is sufficiently flexible to be temporarily distorted into the prefiring configuration shown in FIG. 5. In that configuration, legs 54a and 54b are longitudinally shifted relative to one another and interlocking finger elements 60a and 60b releasably engage each other along planar faces 64a and 64b.

Figure 7A:
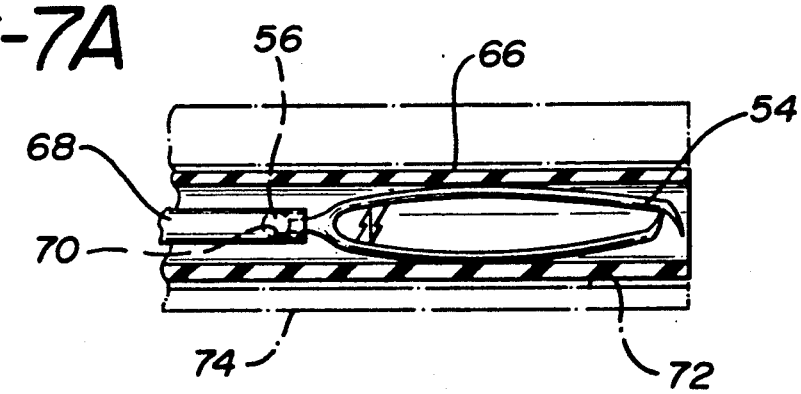
FIGS. 7A-7F are partially schematic, partial perspective views, taken from the side and on a reduced scale, of an endoscopic stapling device in accordance with the present invention, showing successive steps in the application of the surgical staple of FIGS. 5 and 6 to internal body tissues.

As illustrated in FIG. 7A, staple 54 is disposed in its prefiring configuration inside the distal end of an elongate flexible tubular member 66 distally of an elongate flexible rod member 68 itself slidably inserted in tubular member 66. Staple 54 is releasably attached to rod member 68 by a ball and socket connection comprising knob 56 and a corresponding recess 70 at the distal end of rod 68.

Figure 7B:
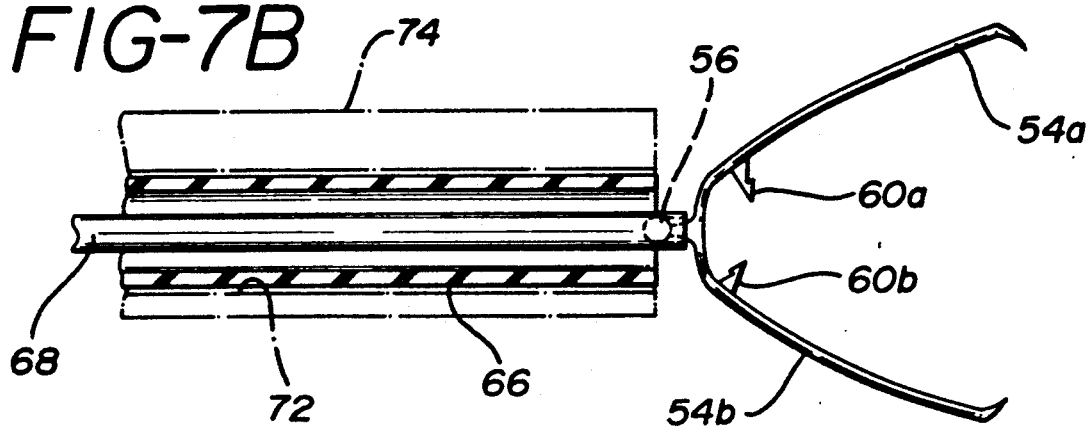
Figure 7C:
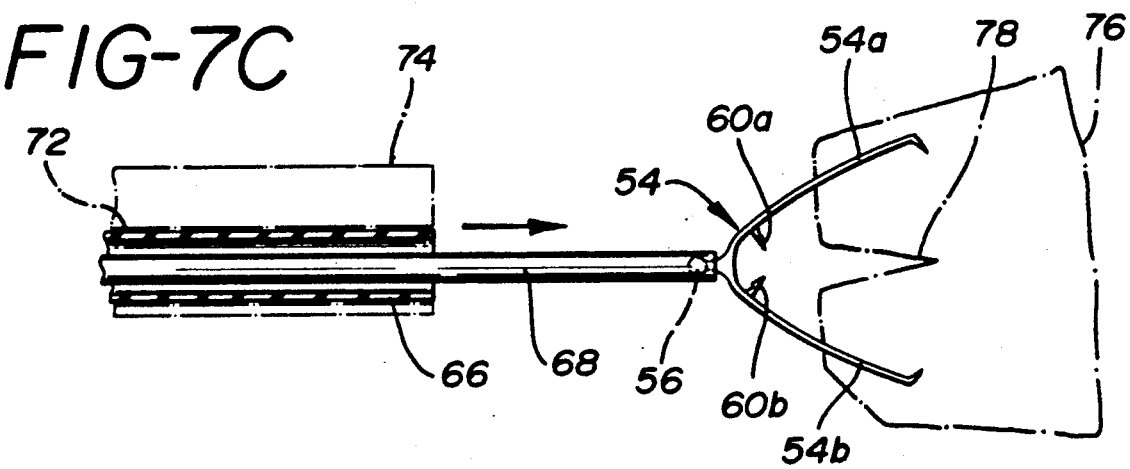

Tubular member 66 has a diameter sufficiently small so that it is slidably insertable into a biopsy channel 72 extending longitudinally through a flexible tubular endoscope member 74. Upon the insertion of the endoscope, with tubular member 66, rod member 68 and staple 54 disposed in the endoscope's biopsy channel, into a patient's body and the location, via the fiberoptics of the endoscope, of an internal site requiring a closure, rod member 68 is shifted in a distal direction to eject staple 54 from tubular member 66. The ejected staple automatically assumes an opened configuration illustrated in FIG. 7B. Further distally directed motion of rod member 68 pushes the opened staple 54 into the internal body tissues 76 of the patient, as shown in FIG. 7C.

Figure 7D:
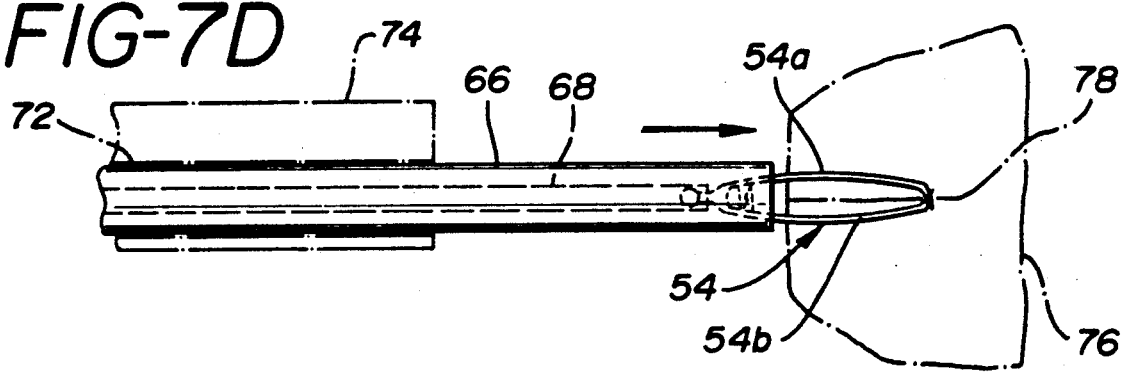
Figure 7E:
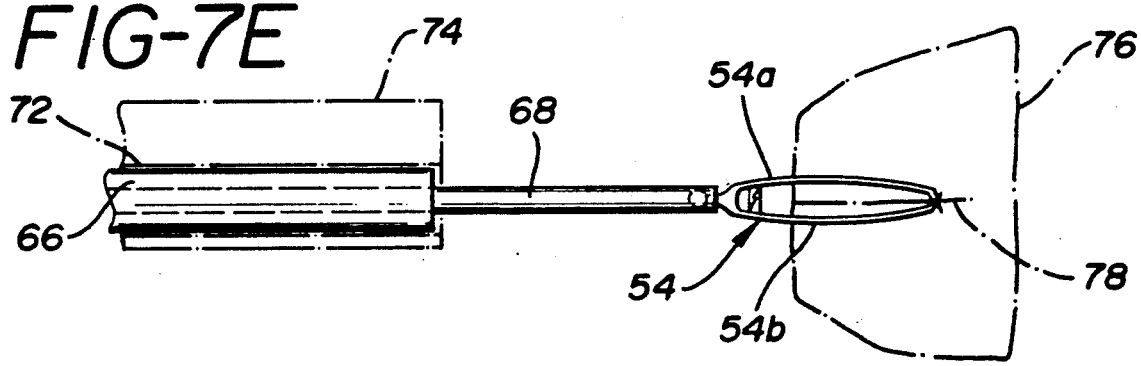
Figure 7F:
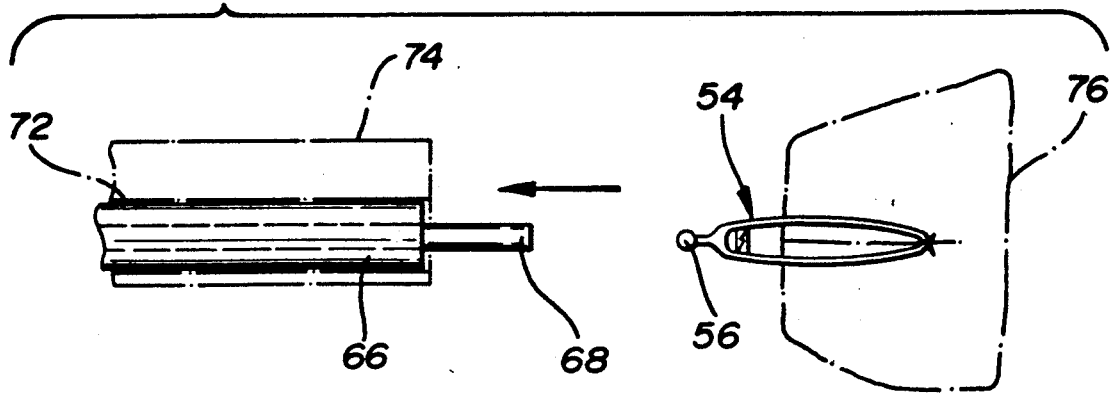

Upon an embedding of staple 54 in body tissues 76 about a cut, tear or other opening 78, tubular member 66 is shifted distally from the endoscope and engages staple legs 54a and 54b to bend them inwardly towards one another in opposition to the internal spring forces of the staple. Upon a sufficient advance of tubular member 66, barbs or hooks 62a and 2b of finger elements 60a and 60b interlock and hold staple legs 54a and 54b in the closed configuration (FIG. 7D). Tubular member 66 is then withdrawn back into the biopsy channel of the endoscope (FIG. 7E). Finally, as depicted in FIG. 7F, rod member 68 is retracted and the endoscope removed from the patient's body.

In an alternative series of steps, rod member 68 is retracted prior to the withdrawal of tubular member 66. In that procedure, tubular member 66 serves to hold staple 54 against the return stroke of rod member 68 and facilitates the removal of knob 56 from recess 70. Usually, however, it is contemplated that the forces holding the ball and socket joint together are smaller than the forces retaining staple 54 in body tissues 76 so that there will be no problem retracting rod member 68 subsequently to the withdrawal of tubular member 66.

As illustrated in FIGS. 8A–8F, another endoscopic stapling device 80 similar to the device of FIGS. 7A–7F includes an outer elongate flexible tubular member 82 having a diameter sufficiently small so that the tubular member is slidably insertable into a biopsy channel 84 extending longitudinally through a flexible tubular endoscope member 86. Endoscopic stapling device 80 further comprises an inner elongate flexible tubular member 88 slidably disposed inside tubular member 82 and an elongate flexible rod member 90 slidably disposed inside inner tubular member 88. In the prefiring configuration of FIG. 8A, a staple 91 (similar to staple 54) is disposed in a closed configuration at least partially inside inner tubular member 88 distally of a distal end of rod member 90. Staple 91 is releasably attached to rod member 90 by a ball and socket connection comprising a knoblike projection 92 on the staple and a corresponding recess 93 at the distal end of rod 90.

Outer tubular member 82 is provided at a distal end with a forceps 94 including a pair of metal jaws 94a and 94b which are spring biased towards a spread-apart state by virtue of their own internal microstructure.

Figure 8A:
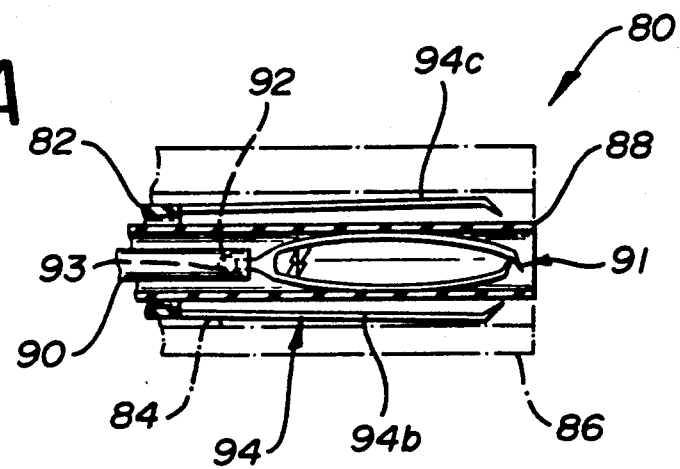
FIGS. 8A-8F are partially schematic, partial perspective views, similar to FIGS. 8A-8F, of another endoscopic stapling device in accordance with the present invention, showing successive stages in the application of the surgical staple of FIGS. 5 and 6 to internal body tissues.

FIG. 8A shows endoscopic stapling device 80 in a prefiring configuration in which outer tubular member 82 including forceps jaws 94a and 94b, inner tubular member 88, rod 90 and staple 91 are all located in biopsy channel 84 of endoscope 86. More specifically, staple 91 is disposed in a closed prefiring configuration (see FIG. 5) distally of rod member 30 and inside tubular member 28 at the distal end thereof.

Figure 8B:
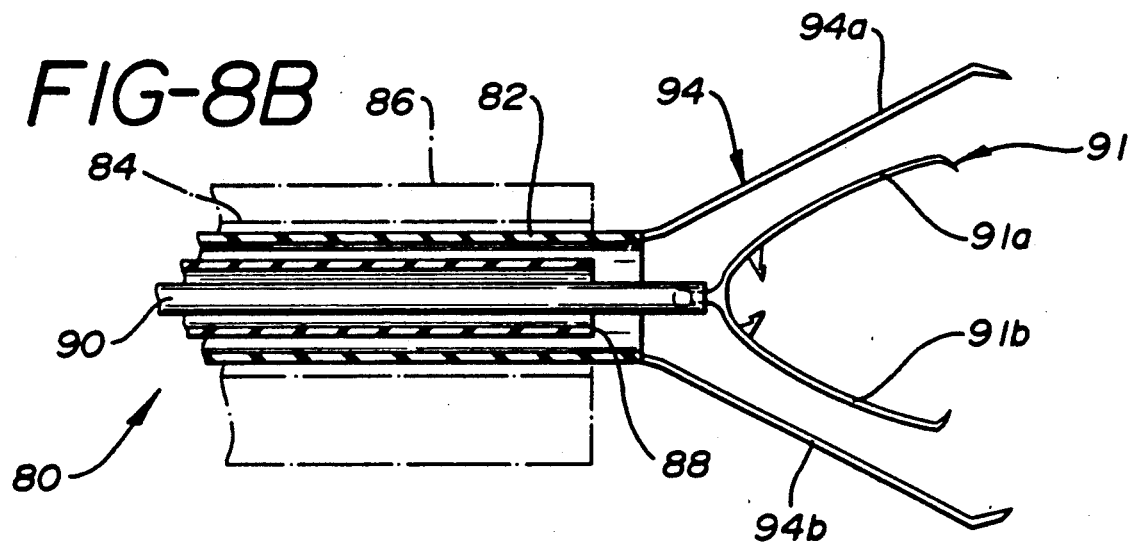
Figure 8C:
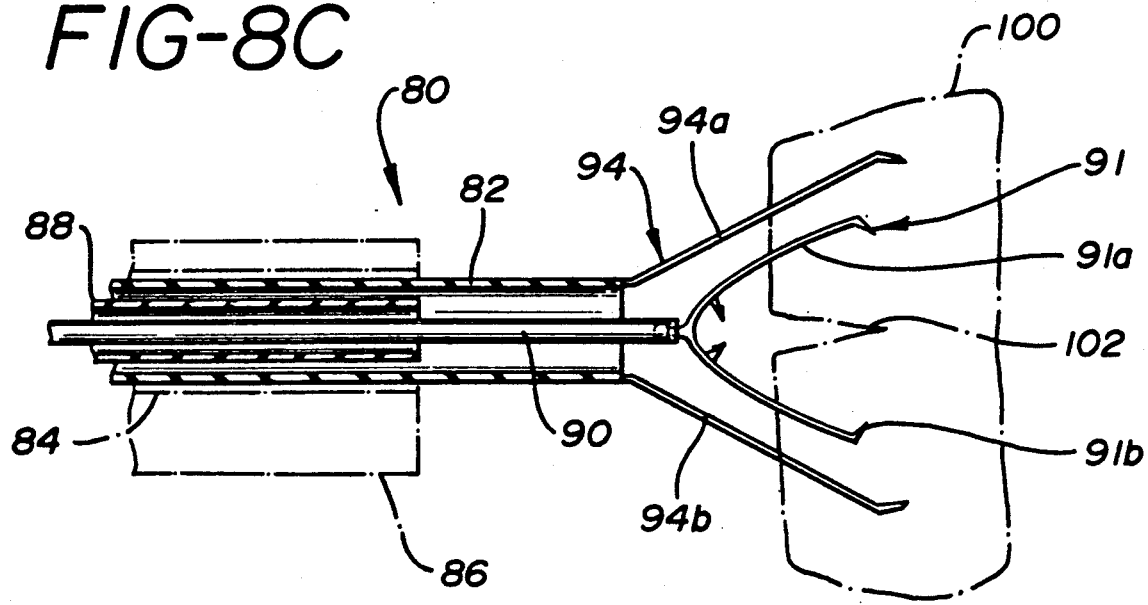

Endoscope 86 is inserted through an aperture (not illustrated) in a patient's body (not shown) and is used to visually locate in the patient's body the internal body tissues upon which a stapling operation is to be performed. Upon the locating of the surgical site, tubular outer member 82 and rod member 90 are pushed in the distal direction through biopsy channel 84 to open forceps jaws 94a and 94b and to eject staple 91 from tubular member 88, as depicted in FIG. 8B.

In the next step of a surgical procedure using endoscopic stapling device 80, outer tubular member 82 and rod member 90 are pushed further in the distal direction to move opened staple 91 towards internal body tissues 100 having an opening 102 previously detected through the optical pathway (not illustrated) of endoscope 86. FIG. 4C shows forceps jaws 94a and 94b and staple 91 substantially embedded in the body tissues 100 in a region about opening 102.

Figure 8D:
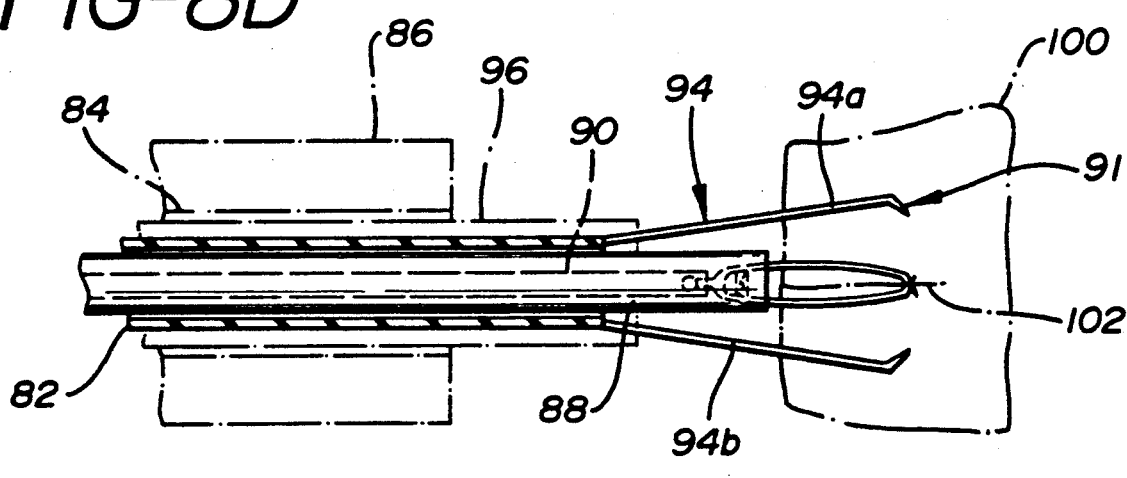
Figure 8E:
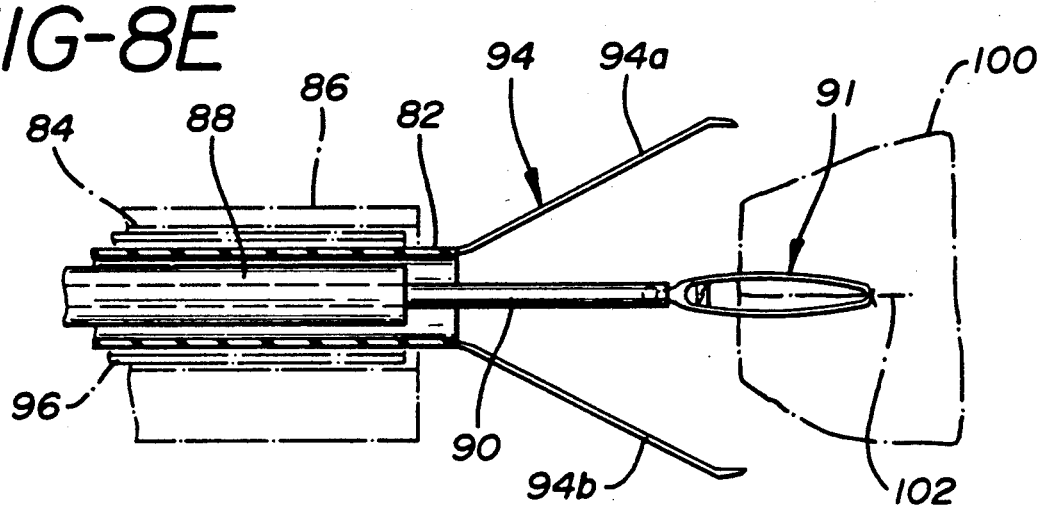
Figure 8F:
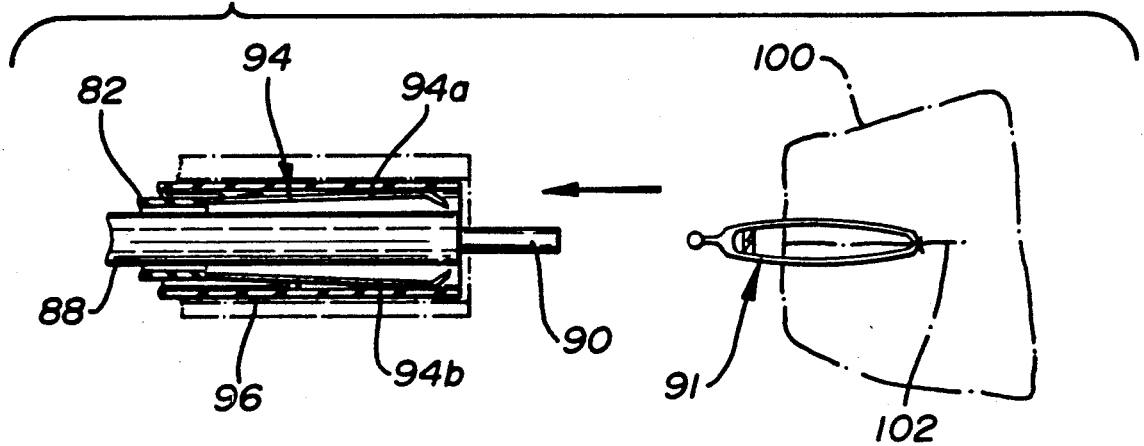
Figure 9:
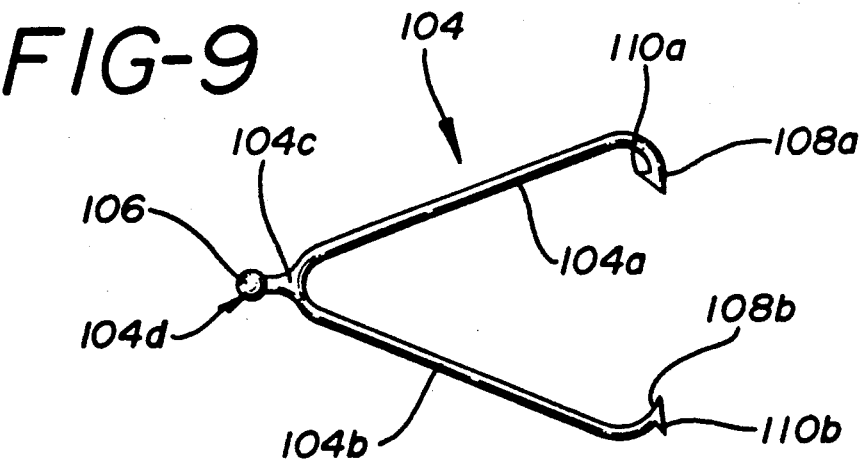
FIG. 9 is a side elevational view of another staple usable in an endoscopic stapling device in accordance with the present invention, showing the staple in an opened configuration.

Upon the embedding of opened staple 91 in internal body tissues 100, inner tubular member 88 is pushed in the distal direction to engage staple legs 91a and 91b and thereby close the staple about opening 102. Simultaneously, as illustrated in FIG. 8D, an additional outer tubular member 96 slidably disposed in biopsy channel 84 around tubular member 82 is shifted distally to engage forceps jaws 94a and 94b and thereby close the forceps 94 to aid in the closure of opening 102 during the stapling operation.

In a subsequent step shown in FIG. 4E, outermost tubular member 96 and inner tubular member 88 are retracted into biopsy channel 84. In addition, tubular member 82 is moved proximally to withdraw forceps 94 from body tissues 100. During the retraction of outer tubular member 82 into the endoscope's biopsy channel, forceps jaws 94a and 94b pivot towards one another through a camming action when the jaws slide past the rim or lip at the distal end of biopsy channel 84 or past the mouth of outermost tubular member 96. Finally, rod member 90 is retracted into inner tubular member 88 (FIG. 4F) and the entire endoscopic stapling device is then withdrawn from the patient's body through the aperture through which it was introduced.

Figure 10:
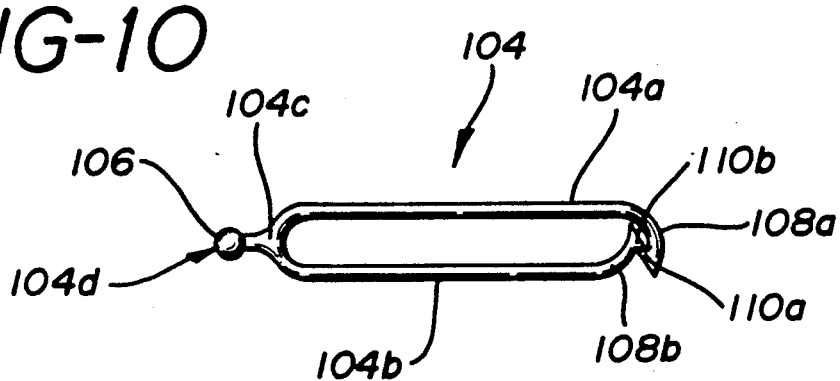
FIG. 10 is a side elevational view of the staple of FIG. 9 in a closed, postfiring configuration.

Another staple 104 usable in an endoscopic stapling device in accordance with the present invention is illustrated in FIGS. 9-12. That staple includes includes a pair of legs 104a and 104b joined by a bight section 104c and provided on a side of the bight section opposite the legs with a projection 104d terminating in a knob or ball 106. Each leg 104a and 104b is provided at a free end with a respective inwardly turned foot 108a and 108b. Foot 108a is formed on an outer, distally facing side with a barb or hook 110a, while foot 108b is provided on an inwardly or proximally facing face with another barb or hook 110b. As illustrated in FIG. 10, hooks 110a and 110b interfit and thereby cooperate with one another to lock the staple in a closed configuration at the end of a stapling operation.

Like legs 54a and 54b of staple 54, legs 104a and 104b of staple 104 are spring biased outwardly. Thus, a force pressing legs 104a and 104b towards one another is required to close staple 104.

Figure 11:
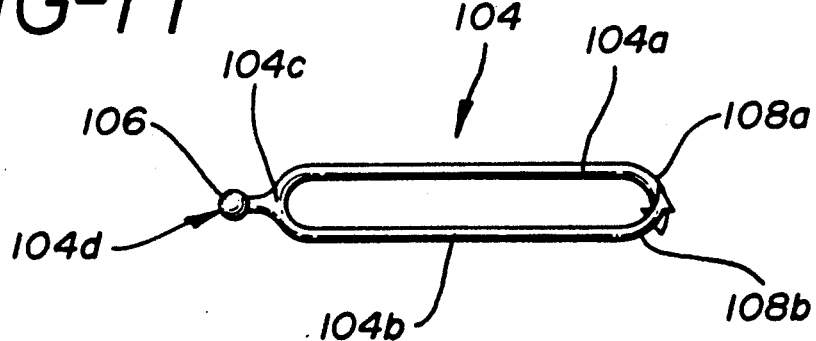
FIG. 11 is a side elevational view of the staple of FIGS. 9 and 10, showing the staple in a closed, prefiring configuration.
Figure 12:
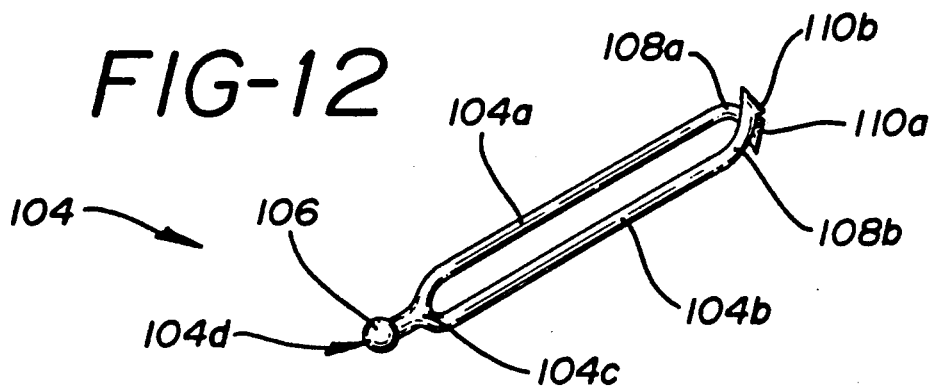
FIG. 12 is a rear perspective view of the staple of FIGS. 9–11, showing the staple in the closed, prefiring configuration.

FIGS. 11 and 12 show staple 104 in the prefiring closed configuration. The staple legs 104a and 104b are disposed side-by-side. When staple 104 is opened upon ejection from a tubular member pursuant to the invention, legs 104a and 104b spring apart under the action of internal forces (FIG. 9) so that hooks 110a and 110b are aligned with one another.

The staple of FIGS. 9-12 is particularly useful in closing tubular body organs such as blood vessels, sperm ducts, and Fallopian tubes.

Figure 13:
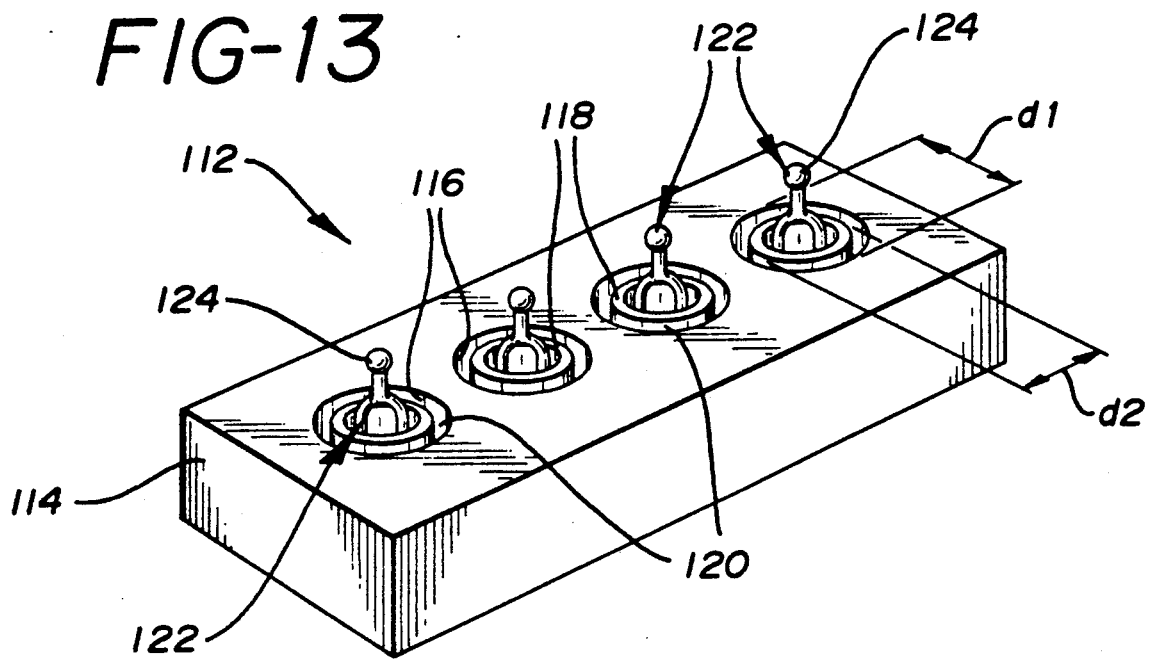
FIG. 13 is an isometric view of a staple package in accordance with the present invention.

As depicted in FIG. 13, a surgical staple package 112 comprises a container 114 provided with a plurality of cylindrical recesses 116 having a common diameter d1. Disposed in each recess 116 is a respective annular sleeve 118. Sleeves 118 have a common outside diameter d2 smaller than diameter d1 of recesses 116, whereby an annular space 120 is formed between each sleeve 118 and the cylindrical wall defining the respective recess 116. A plurality of staples 122 are seated in sleeves 118, each staple 122 being provided with a connector element 124 in the form of a knob, a plate or other cross-sectionally polygonal member for releasably connecting the respective staple to the distal end of a flexible rod member 30, 68, 90 of an endoscopic stapling device. Staples 122, whether in the specific form of staple 32, 54, or 104 or some other form consistent with the principles of the invention, are placed in a prefiring closed configuration in sleeve 118.

Figure 14:
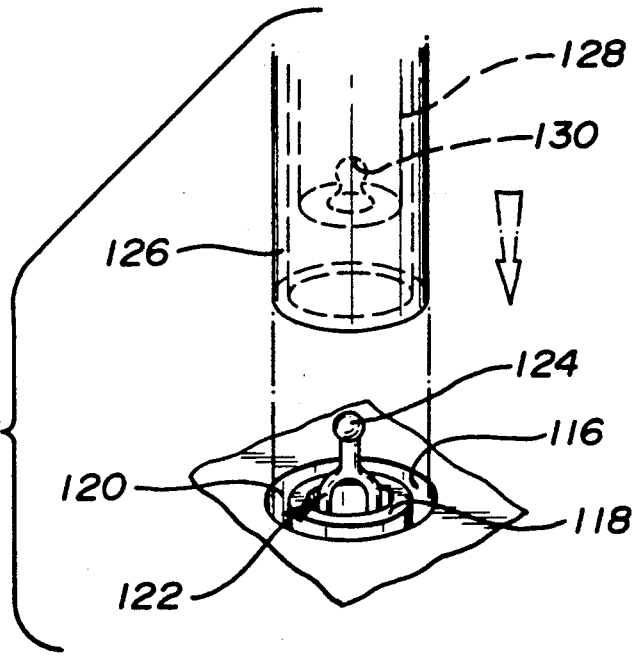
FIGS. 14 and 15 are essentially isometric views of a staple in the package of FIG. 13, showing successive steps in the removal of the staple from the package and the simultaneous loading of the staple into an endoscopic stapling device in accordance with the present invention.
Figure 15:
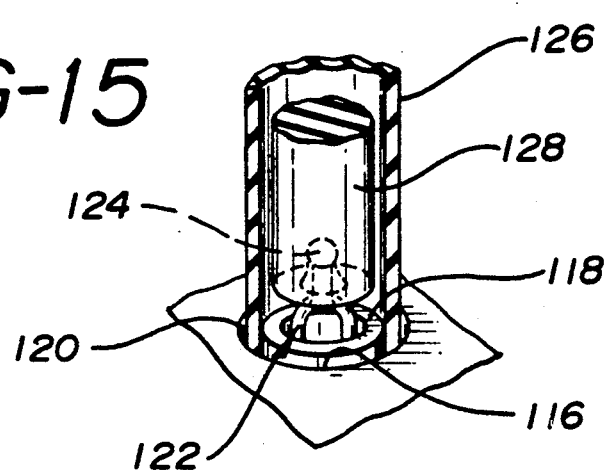

Annular spaces 120 have a width and a diameter sufficiently large so that the annular spaces can each receive the distal end of an inner tubular member 28, 66, 88 of an endoscopic stapling device in accordance with the invention. As illustrated in FIGS. 14 and 15, to load a staple 122 from package 112, the distal end of a flexible tubular member 126 of an endoscopic stapling device in accordance with the invention is inserted into the annular space 120 about the respective staple. Subsequently, a flexible rod member 128 of the endoscopic stapling device is moved distally through tubular member 126 until a recess 130 at the distal end of rod member 128 receives connector element 124, releasably securing the staple 122 to rod member 128. Tubular member 126 is then withdrawn from the annular space 120 and the staple 122 removed from its respective sleeve 118. The entire endoscopic stapling device is then inserted into the biopsy channel of an endoscope. It is to be understood that, should the need arise for more than one staple to close an internal opening, an endoscopic stapling device in accordance with the invention may be removed from the endoscope's biopsy channel and reloaded with another staple while the endoscope remains partially inserted in the patient's body.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

We claim:

1. A surgical instrument comprising:
   an endoscope including an elongate flexible outer tubular member and a biopsy channel extending longitudinally through said tubular member;
   an elongate flexible inner tubular member slidably disposed in said biopsy channel;
   an elongated flexible rod member slidably disposed inside said inner tubular member;
   a staple disposed in a closed configuration at least partially inside said inner tubular member distally of a distal end of said rod member; and
   means for opening said staple upon an ejection thereof from said inner tubular member by a distally directed motion of said rod member, said staple being provided with means for locking said staple in a closed configuration upon a closing of said staple by a distally directed motion of said inner tubular member subsequent to a distally directed motion of said rod member pushing said staple, in an opened configuration thereof, into or about body tissues to be clamped by said staple.

2. The surgical instrument set forth in claim 1 wherein said means for opening includes a spring bias construction of said staple.

3. The surgical instrument set forth in claim 1 wherein said staple has a pair of legs joined by a bight portion, said means for locking includes a pair of interlocking hook elements on said legs.

4. The surgical instrument set forth in claim 3 wherein said interlocking hook elements are disposed at the distal ends of said legs.

5. The surgical instrument set forth in claim 3 wherein said interlocking hook elements are disposed proximally of the distal ends of said legs.

6. The surgical instrument set forth in claim 1, further comprising means for releasably attaching a proximal end of said staple to a distal end of said rod member.

7. The surgical instrument set forth in claim 6 wherein said staple includes a pair of arcuate legs joined at their proximal ends by a bight, said means for releasably attaching being formed in part at said bight.

8. The surgical instrument set forth in claim 7 wherein said means for releasably attaching includes a linear projection extending in a proximal direction from said bight in a prefiring configuration of said staple.

9. The surgical instrument set forth in claim 8 wherein said means for releasably attaching further includes a longitudinally extending recess in said distal end of said rod member.

10. The surgical instrument set forth in claim 8 wherein said projection is planar and said recess is polygonal in transverse cross-section.

11. The surgical instrument set forth in claim 1, further comprising first actuator means operatively connected to said flexible inner tubular member for sliding same through said biopsy channel, also comprising second actuator means operatively connected to said flexible rod member for sliding same through said flexible inner tubular member.

12. A surgical stapling instrument comprising:
an elongate flexible tubular member having a diameter sufficiently small so that said tubular member is slidably insertable into a biopsy channel extending longitudinally through a flexible tubular endoscope member;
an elongate flexible rod member slidably disposed inside said elongate flexible tubular member;
a staple disposed in a closed configuration at least partially inside said elongate flexible tubular member distally of a distal end of said rod member; and
means for opening said staple upon an ejection thereof from said inner tubular member by a distally directed motion of said rod member, said staple being provided with means for locking said staple in a closed configuration upon a closing of said staple by a distally directed motion of said inner tubular member subsequent to a distally directed motion of said rod member pushing said staple, in an opened configuration thereof, into or about body tissues to be clamped by said staple.

13. The surgical stapling instrument set forth in claim 12 wherein said means for opening includes a spring bias construction of said staple.

14. The surgical stapling instrument set forth in claim 12 wherein said staple has a pair of legs joined by a bight portion, said means for locking includes a pair of interlocking hook elements on said legs.

15. The surgical stapling instrument set forth in claim 14 wherein said interlocking hook elements are disposed at the distal ends of said legs.

16. The surgical stapling instrument set forth in claim 14 wherein said interlocking hook elements are disposed proximally of the distal ends of said legs.

17. The surgical stapling instrument set forth in claim 12, further comprising means for releasably attaching a proximal end of said staple to a distal end of said rod member.

18. The surgical instrument set forth in claim 17 wherein said staple includes a pair of arcuate legs joined at their proximal ends by a bight, said means for releasably attaching being formed in part at said bight.

19. The surgical stapling instrument set forth in claim 18 wherein said means for releasably attaching includes a linear projection extending in a proximal direction from said bight in a prefiring configuration of said staple.

20. The surgical stapling instrument set forth in claim 19 wherein said means for releasably attaching further includes a longitudinally extending recess in said distal end of said rod member.

21. The surgical stapling instrument set forth in claim 19 wherein said projection is planar and said recess is polygonal in transverse cross-section.

22. The surgical instrument set forth in claim 12, further comprising first actuator means operatively connected to said flexible tubular member for sliding same through said biopsy channel, also comprising second actuator means operatively connected to said flexible rod member for sliding same through said flexible elongate flexible tubular member.

23. A surgical instrument comprising:
an endoscope including an elongate flexible outer tubular member and a biopsy channel extending longitudinally through said tubular member;
an elongate flexible inner tubular member slidably disposed in said biopsy channel;
an elongate flexible rod member slidably disposed inside said inner tubular member;
a staple disposed in a closed configuration at least partially inside said inner tubular member distally of a distal end of said rod member; and
means for opening said staple upon an ejection thereof from said inner tubular member by a distally directed motion of said rod member, said means for opening including an additional flexible tubular member slidably disposed in said biopsy channel, said additional flexible tubular member being provided at a distal end with a pair of forceps jaws releasably connected to legs of said staple.

24. The surgical instrument set forth in claim 23, wherein said jaws are provided on inwardly facing surfaces with grooves, said legs being seated in said grooves in a closed configuration of said staple and said forceps jaws.

25. The surgical instrument set forth in claim 24 wherein said jaws are provided at their free ends with respective recesses, free ends of said legs being held in said recesses in said closed configuration of said staple and said forceps jaws.

26. The surgical instrument set forth in claim 23 wherein said additional tubular member is disposed around said inner tubular member.

27. The surgical instrument set forth in claim 23 wherein said staple is provided with means for locking said staple in a closed configuration upon a closing of said staple by a distally directed motion of said inner tubular member subsequent to a distally directed motion of said rod member pushing said staple, in a opened configuration thereof, into or about body tissues to be clamped by said staple.

28. The surgical instrument set forth in claim 27 wherein said staple has a pair of legs joined by a bight portion, said means for locking includes a pair of interlocking hook elements on said legs.

29. A surgical stapling instrument comprising:
an elongate flexible tubular member having a diameter sufficiently small so that said tubular member is slidably insertable into a biopsy channel extending longitudinally through a flexible tubular endoscope member;
an elongate flexible rod member slidably disposed inside said elongate flexible tubular member;
a staple disposed in a closed configuration at least partially inside said elongate flexible tubular member distally of a distal end of said rod member; and
means for opening said staple upon an ejection thereof from said inner tubular member by a distally directed motion of said rod member, said means for opening including an additional flexible tubular member around said elongate flexible tubular member, said additional flexible tubular member being provided at a distal end with a pair of forceps jaws releasably connected to legs of said staple.

30. The surgical stapling instrument set forth in claim 29 wherein said jaws are provided on inwardly facing surfaces with grooves, said legs being seated in said grooves in a closed configuration of said staple and said forceps jaws.

31. The surgical stapling instrument set forth in claim 30 wherein said jaws are provided at their free ends with respective recesses, free ends of said legs being held in said recesses in said closed configuration of said staple and said forceps jaws.

32. The surgical instrument set forth in claim 29 wherein said staple is provided with means for locking said staple in a closed configuration upon a closing of said staple by a distally directed motion of said inner tubular member subsequent to a distally directed motion of said rod member pushing said staple, in an opened configuration thereof, into or about body tissues to be clamped by said staple.

33. The surgical instrument set forth in claim 32 wherein said staple has a pair of legs joined by a bight portion, said means for locking includes a pair of interlocking hook elements on said legs.

34. A surgical instrument comprising:
an endoscope including an elongate flexible outer tubular member and a biopsy channel extending longitudinally through said tubular member;
an elongate flexible rod member slidably disposed inside said tubular member;
a staple disposed in a closed configuration at least partially inside said tubular member distally of a distal end of said rod member;
means for opening said staple upon an ejection thereof from said tubular member by a distally directed motion of said rod member; and
means for closing said staple while maintaining a force on said staple pushing into tissue to be stapled.

35. The surgical instrument set forth in claim 34 wherein said means for closing includes an elongate flexible inner tubular member slidably disposed in said biopsy channel, said rod member being disposed inside said inner tubular member, said staple being disposed in a closed configuration at least partially inside said inner tubular member distally of a distal end of said rod member.

* * * * *

UNITED STATES PATENT AND TRADEMARK OFFICE
CERTIFICATE OF CORRECTION

PATENT NO. : 5,015,249

DATED : May 14, 1991

INVENTOR(S) : Naomi L. Nakao and Peter J. Wilk

It is certified that error appears in the above-identified patent and that said Letters Patent is hereby corrected as shown below:

Column 4, line 14, change "than" to -- that --; line 68, change "8A-8F" to -- 7A-7F --.

Column 8, line 66, change "4C" to -- 8C --.

Column 9, line 11, change "4E" to -- 8E --; line 22, change "4F" to -- 8F --.

Column 12, line 24, delete "flexible".

Signed and Sealed this

Eleventh Day of January, 1994

Attest:

BRUCE LEHMAN

Attesting Officer

Commissioner of Patents and Trademarks